United States Patent
Bharat et al.

(10) Patent No.: US 9,259,155 B2
(45) Date of Patent: Feb. 16, 2016

(54) METHOD TO ESTIMATE INTERFRACTIONAL AND INTRAFRACTIONAL ORGAN MOTION FOR ADAPTIVE EXTERNAL BEAM RADIOTHERAPY

(75) Inventors: Shyam Bharat, Ossining, NY (US); Vijay Parthasarathy, Tarrytown, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 53 days.

(21) Appl. No.: 14/237,227

(22) PCT Filed: Jul. 24, 2012

(86) PCT No.: PCT/IB2012/053752
§ 371 (c)(1),
(2), (4) Date: Feb. 5, 2014

(87) PCT Pub. No.: WO2013/024380
PCT Pub. Date: Feb. 21, 2013

(65) Prior Publication Data
US 2014/0193058 A1 Jul. 10, 2014

Related U.S. Application Data

(60) Provisional application No. 61/523,887, filed on Aug. 16, 2011, provisional application No. 61/602,112, filed on Feb. 23, 2012.

(51) Int. Cl.
*G01T 1/08* (2006.01)
*A61N 5/10* (2006.01)
(Continued)

(52) U.S. Cl.
CPC .............. *A61B 5/0033* (2013.01); *A61N 5/103* (2013.01); *A61N 5/1037* (2013.01);
(Continued)

(58) Field of Classification Search
None
See application file for complete search history.

(56) References Cited

U.S. PATENT DOCUMENTS 4,972,836 A   11/1990  Schenck et al.
5,241,300 A    8/1993  Buschmann
(Continued)

FOREIGN PATENT DOCUMENTS

WO    2011009087 A1    1/2011

OTHER PUBLICATIONS

Kim, D., et al.; Dissolvable films of silk fibroin for ultrathin conformal bio-integrated electronics; 2010; Nature Materials; 9:511-517.
(Continued)

*Primary Examiner* — Utpal Shah

(57) ABSTRACT

A therapy system (10) includes one or more processors (98, 100). The processors (98, 100) are programmed to receive one or more of: (1) dosimetric data from dosimeters (26, 28, 202, 204, 206, 208, 210, 212) implanted within a patient and/or positioned on a vest (200); and (2) motion data from surrogates (18, 20, 22, 24) implanted within the patient. Based on the motion data, a current location and/or shape of a surrogate (18, 20, 22, 24) is determined and deviations between the current location and/or shape and a reference location and/or shape are determined. Based on the dosimetric data, a delivered dose distribution is compared with a planned dose distribution and deviations therebetween are determined. The deviations determined from the motion data and/or the dosimetric data are employed for adaptive planning, alignment, post treatment analysis, and safety.

21 Claims, 6 Drawing Sheets

(51) Int. Cl.
*A61B 5/00* (2006.01)
*A61B 5/11* (2006.01)

(52) U.S. Cl.
CPC .......... *A61N 5/1049* (2013.01); *A61N 5/1071* (2013.01); *G01T 1/08* (2013.01); *A61B 5/1126* (2013.01); *A61B 5/721* (2013.01); *A61B 2562/0233* (2013.01); *A61N 5/1038* (2013.01); *A61N 5/1039* (2013.01); *A61N 2005/1051* (2013.01); *A61N 2005/1072* (2013.01); *G06T 2207/30004* (2013.01)

(56) References Cited

U.S. PATENT DOCUMENTS

| | | | |
|---|---|---|---|
| 5,321,257 | A | 6/1994 | Danisch |
| 6,256,090 | B1 | 7/2001 | Chen et al. |
| 6,471,710 | B1 | 10/2002 | Bucholtz |
| 6,495,819 | B1 | 12/2002 | Cerwin et al. |
| 6,846,286 | B2 | 1/2005 | Suzuki et al. |
| 6,888,623 | B2 | 5/2005 | Clements |
| 7,440,087 | B2 | 10/2008 | Froggatt et al. |
| 7,772,541 | B2 | 8/2010 | Froggatt et al. |
| 7,930,065 | B2 | 4/2011 | Larkin et al. |
| 2006/0013523 | A1 | 1/2006 | Childers et al. |
| 2007/0265503 | A1 | 11/2007 | Schlesinger et al. |
| 2008/0149835 | A1* | 6/2008 | Moritake et al. ........... 250/336.1 |
| 2008/0218770 | A1 | 9/2008 | Moll et al. |
| 2008/0262390 | A1 | 10/2008 | Bangera et al. |
| 2009/0099472 | A1 | 4/2009 | Remmert et al. |
| 2011/0166407 | A1* | 7/2011 | Sumanaweera et al. .......... 600/1 |
| 2013/0033700 | A1* | 2/2013 | Hallil .............................. 356/72 |

OTHER PUBLICATIONS

Sandler, H. M., et. al.; Reduction in Patient-reported Acute Morbidity in Prostate Cancer Patients Treated with 81-Gy Intensity-modulated Radiotherapy Using Reduced Planning Target Volume Margins and Electromagnetic Tracking: Assessing the Impact of margin Reduction Study; 2010; Urology; 75(5)1004-1008.

Shechter, G., et al.; Fiber optic based localization; Technical Note PR-TN 2009/00142; 2009 Koninklijke Philips Electronics N.V.

* cited by examiner

METHOD TO ESTIMATE INTERFRACTIONAL AND INTRAFRACTIONAL ORGAN MOTION FOR ADAPTIVE EXTERNAL BEAM RADIOTHERAPY

CROSS REFERENCE TO RELATED APPLICATIONS

This application is a national filing of PCT application Serial No. PCT/IB2012/053752, filed Jul. 24, 2012, published as WO 2013/024380 A1 on Feb. 21, 2013, which claims the benefit of U.S. provisional application Ser. No. 61/523,887 filed Aug. 16, 2011 and U.S. provisional application Ser. No. 61/602,112 filed Feb. 23, 2012, both of which are incorporated herein by reference.

The present application relates generally to radiation therapy. It finds particular application in conjunction with estimating interfraction and intrafraction motion and will be described with particular reference thereto. However, it is to be understood that it also finds application in other usage scenarios and is not necessarily limited to the aforementioned application.

In radiation therapy, spatially targeted doses of radiation are applied to the target, such as tumors, containing cancerous or malignant tissue, of a patient. Growing and rapidly multiplying cancer cells tend to be more susceptible to damage from radiation, as compared with normal cells, such that dosages administrated by proper planning preferentially kill cancerous or malignant tissue. Current clinical workflow in radiation therapy typically involves the use of a single three- or four-dimensional image set to develop a detailed treatment plan, including contours around target and organs at risk (OARs), radiation beam directions, energies, dose constraints, etc. This treatment plan is then delivered over multiple fractions.

One challenge for radiation therapy is interfraction motion (i.e., motion between fractions) and intrafraction motion (i.e., motion during fractions). Ideally, the entire dose for a treatment plan is delivered to the target and no dose is delivered in surrounding normal tissue and/or organs at risk. However, due to interfraction and intrafraction motion, this is typically not possible and deviations between the radiation dose delivered to the patient and the planned radiation dose are common. Hence, treatment plans typically include margins around the target to ensure the target are fully irradiated.

To alleviate the effects of interfraction motion, patients are typically aligned on a treatment couch before a fraction. However, there is typically no realignment during a fraction. Researchers have been investigating different ways of capturing target motion during delivery and relating this information back to the treatment plan for motion compensation (both offline and in real-time).

The motion information can also be employed for hypo fractionation (i.e., a reduction in the number of fractions). Advances in intensity modulated radiation therapy (IMRT) optimization techniques have made it possible to reduce margins given detailed motion information. Reducing margins advantageously allows dose escalation and reduction in the number of fractions. However, care must be taken with hypofractionation to ensure the motion information is sufficiently detailed. Otherwise, target may be underdosed and surrounding normal tissue and/or organs at risk may be overdosed.

Approaches to retrieve motion information can be image based and non-image based. Examples of image-based approaches include cone beam computed tomography (CBCT), fluoroscopy, magnetic resonance imaging (MRI), ultrasound, and so on. Examples of non-image-based approaches include electromagnetic (EM) tracking of transponders implanted apriori in the target and so on. EM tracking tracks passive EM transponders that are implanted in the patient.

Known image-based approaches of interrogating motion typically have the benefit of providing high spatial resolution. However, they also have various drawbacks. CBCT only provides interfractional motion information, since it is utilized prior to fraction delivery. Further, due to the additional dose deposition associated with its use, it is often used sparingly, such as on a weekly basis. Hence, it offers poor temporal resolution. Fluoroscopy offers the possibility of high temporal resolution. However, like CBCT, it is associated with an additional dose deposition and is used sparingly. Therefore, it too offers poor temporal resolution. Ultrasound is real-time and adequately sampled spatially, but suffers from relatively poor image quality. MRI offers high spatial resolution and temporal resolution, but is expensive.

Known non-image-based approaches of interrogating motion typically have the benefit of providing high temporal resolution. However, they also have various drawbacks. EM tracking provides a temporal resolution of approximately 10 Hz. However, it suffers from poor spatial resolution since it typically uses between one and three transponders to gather spatial information of the target. Additionally, it provides no spatial information regarding surrounding normal tissue and/or organs at risk.

In view of the foregoing deficiencies with known approaches for retrieving motion information, there is a need for an approach that provides motion information that is adequately sampled both spatially and temporally at all times during treatment. The present application provides a new and improved system and method which overcomes the above-referenced problems and others.

In accordance with one aspect, a therapy system includes at least one processor. The processor is programmed to receive a planning image of a region of a subject. The subject includes a target and/or an organ at risk (OAR), and the subject is associated with at least one surrogate and/or a dosimeter. The surrogate acts as a surrogate for the target and/or the OAR. The dosimeter measures dose delivered to the target and/or the OAR. A reference location and shape in the planning image are determined for each of the target and/or the OAR, and a reference location and/or shape is determined from the planning image of each of the surrogate and/or the dosimeter. The processor is further programmed to determine deviations between one or more of the reference location and/or shape of the surrogate and a current location and/or shape of the surrogate, and a planned dose distribution and a delivered dose distribution, the delivered dose distribution determined from dosimetric data and the reference location and/or shape of the dosimeter.

In accordance with another aspect, a therapy system includes a structure which carries one or more dosimeters, the dosimeters positioned to measure dose delivered to a target and/or an organ at risk (OAR) of a subject. The system further includes at least one processor programmed to: receive dosimetric data indicating dose delivered to the target and/or the OAR from the dosimeters; and determine deviations between a planned dose distribution and a delivered dose distribution, the delivered dose distribution determined from the dosimetric data.

In accordance with another aspect, a method for radiation therapy includes receiving a planning image of a region of a subject. The subject includes a target and/or an organ at risk (OAR) and is associated with at least one surrogate and/or a dosimeter. The surrogate acts as a surrogate for the target and/or the OAR, and the dosimeter measures dose delivered to the target and/or the OAR. A reference location and shape is determined in the planning image for each of the target and/or the OAR. A reference location and/or shape is determined from the planning image of each of the surrogate and/or the dosimeter. Deviations between one or more of: (1) the reference location and/or shape of the surrogate and a current location and/or shape of the surrogate; and (2) a planned dose distribution and a delivered dose distribution are determined. The delivered dose distribution is determined from dosimetric data and the reference location and/or shape of the dosimeter.

In accordance with another aspect, a therapy system includes a structure which carries one or more dosimeters and at least one processor. The dosimeters are positioned to coincide with beams of a therapy delivery apparatus and the processor is programmed to: (1) receive dosimetric data indicating dose delivered to the target and/or the OAR from the dosimeters; and (2) determine deviations between a planned dose distribution and a delivered dose distribution. The delivered dose distribution is determined from the dosimetric data.

In accordance with another aspect, a therapy system includes at least one processor programmed to receive a planning image of a region of a subject. The subject includes a target and/or an organ at risk (OAR), and an implanted optical fiber which defines an optical fiber structure (OFS) acting as a surrogate for the target and/or the OAR. A reference location and shape is determined in the planning image for each of the target and/or the OAR. Reference optical motion data indicating a reference location and shape of the OFS is received and the reference location and shape of the OFS is determined in the planning image from the reference optical motion data. Current optical motion data indicating a current location and shape of the OFS is received and the current location and shape of the OFS is determined in the planning image from the current optical motion data. Deviations between the determined reference location and shape of the OFS and the determined current location and shape of the OFS are determined.

One advantage resides in more accurate tracking of targets and/or organs at risk.

Another advantage resides in tracking a target and/or organ at risk with high temporal resolution.

Another advantage resides in tracking a target and/or organ at risk with high spatial resolution.

Another advantage resides in hypo fractionation (reduced number of fractions).

Another advantage resides in reduced margins.

Another advantage resides in verification of the dose distribution delivered to the patient.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
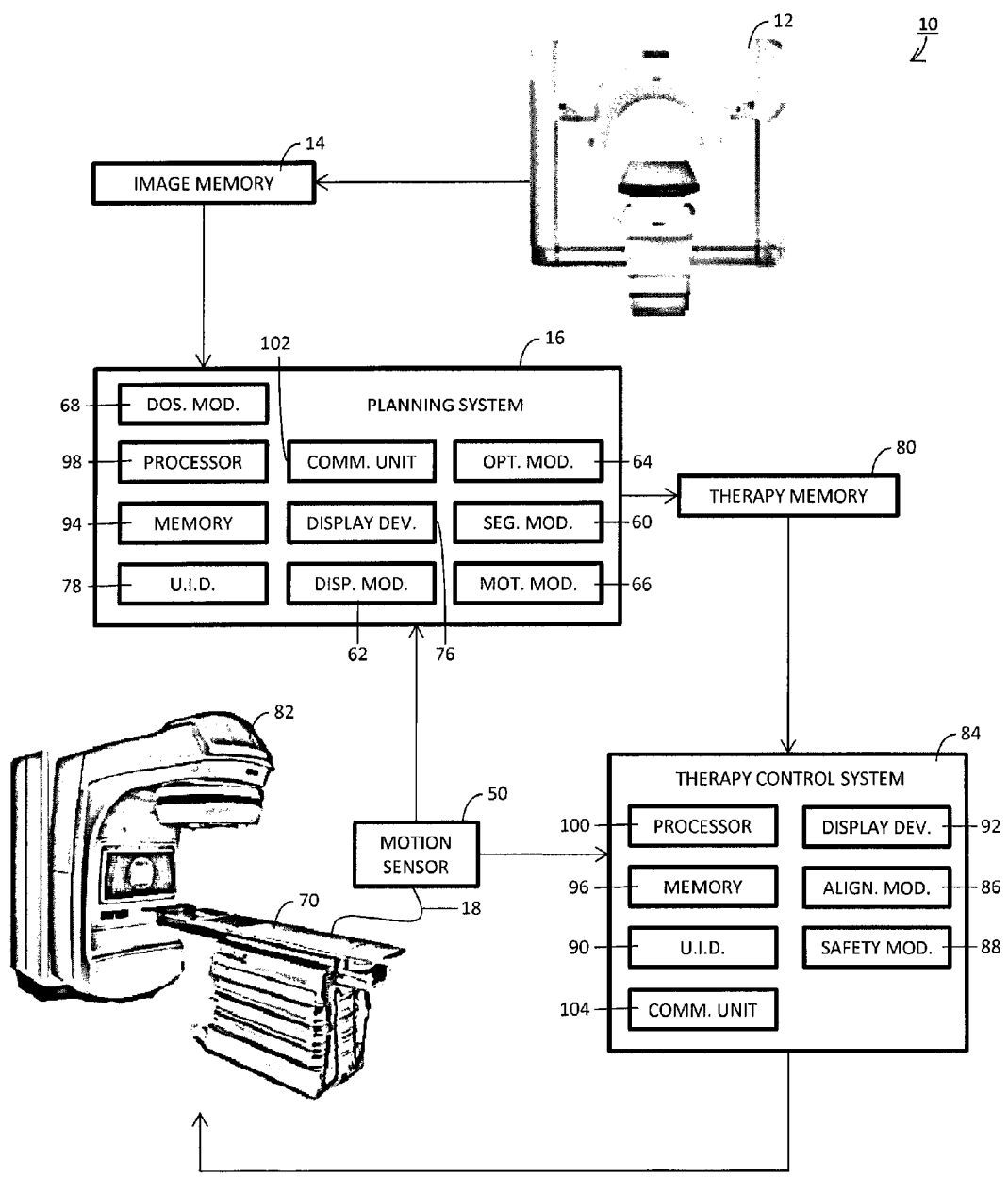
FIG. 1 illustrates a therapy system in accordance with aspects of the present disclosure.

With reference to FIG. 1, a therapy system 10 includes one or more imaging modalities 12 for acquiring images of targets and/or organs at risk within patients. The imaging modalities 12 suitably include one or more of a computed tomography (CT) scanner, a positron emission tomography (PET) scanner, a magnetic resonance (MR) scanner, a single photon emission computed tomography (SPECT) scanner, a cone-beam computed tomography (CBCT) scanner, and the like. Images acquired from the imaging modalities 12 are stored in one or more image memories 14.

A planning system 16 of the therapy system 10 receives one or more planning images, such as three- and/or four-dimensional image sets, of targets and/or organs at risk for patients. Typically, the planning images are received from the imaging modalities 12 via the image memories 14, but other sources are contemplated. As discussed hereafter, the planning images are employed by the planning system 16 to generate and/or update treatment plans.

Figure 2:
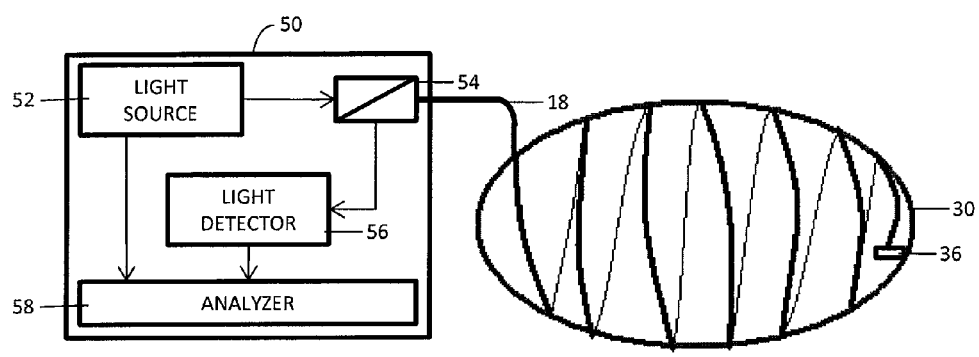
FIG. 2 illustrates an optical fiber acting as a surrogate for a target.
Figure 3:
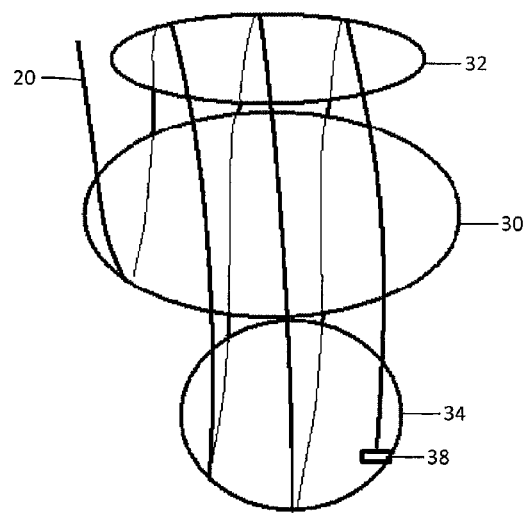
FIG. 3 illustrates an optical fiber acting as a surrogate for a target and organs at risk.
Figure 4:
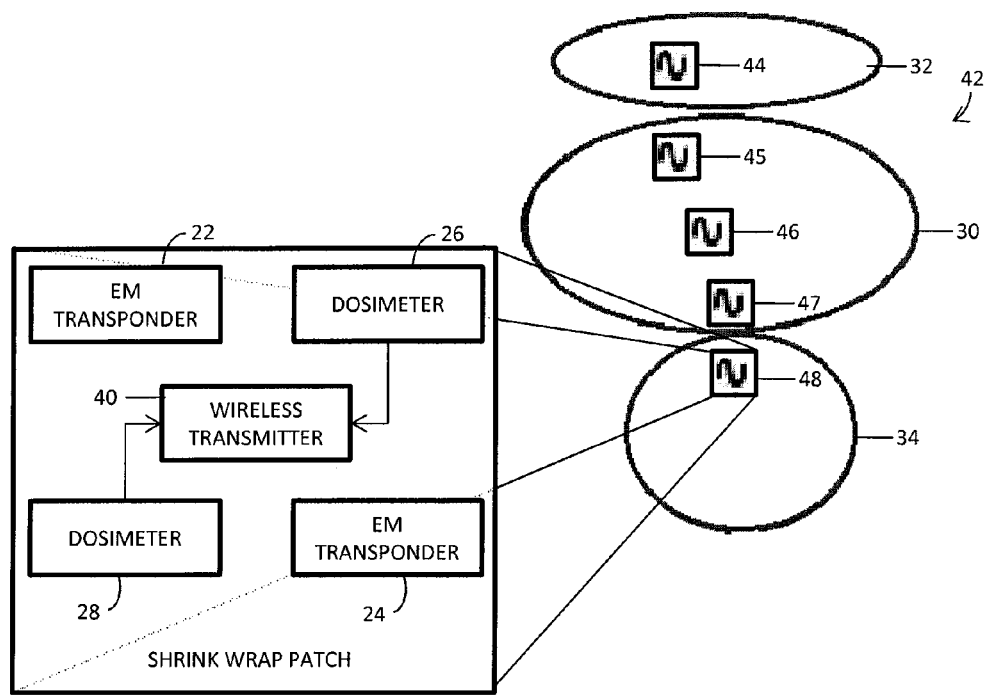
FIG. 4 illustrates a shrink wrap positioned on a target.

As shown in FIGS. 2-4, prior to generating the planning images for a patient, typically one or more surrogates 18, 20, 22, 24 and/or one or more dosimeters 26, 28 are implanted within the patient. The surrogates 18, 20, 22, 24 are implanted within the patient in a pattern which defines a motion structure (MS). The shape of the MS is defined by the shape of the surrogates 18, 20, 22, 24 and/or the spatial relationship between the surrogates 18, 20, 22, 24. The surrogates 18, 20, 22, 24 act as surrogates for a target 30 and/or one or more organs at risk (OARs) 32, 34 of the patient. The target 30 is an organ or other tissue region which contains the tumor to be treated by the radiation beam. The dosimeters 26, 28 can be, for example, silicon diodes, metal oxide semiconductor field effect transistors (MOSFETs), and other like electronic point dosimeters. MOSFET dosimeters can have a footprint of around 2 mm. The surrogates 18, 20, 22, 24 can be, for example, optical fibers 18, 20 and/or electromagnetic (EM) transponders 22, 24. Each of the optical fibers 18, 20 includes a mirror 36, 38 at the end of the optical fiber.

In some embodiments, the optical fibers 18, 20 include multiple fibers, each representing a target and/or one or more OARs of the patient. Further, in some embodiments, the optical fibers 18, 20 include one or more fiber groups of a plurality of fibers, each group representing a target and/or one or more OARs of the patient. The level of surgical difficulty and the properties of the optical fibers 18, 20 dictate the spatial positioning and shapes of the optical fibers 18, 20. Fiber loops of 10-15 mm or 30-50 mm in diameter are contemplated.

With reference to the examples of FIGS. 2 and 3, the optical fibers 18, 20 are implanted within the patient in a pattern which defines the MS and act as surrogates for the target 30 and/or the OARs 32, 34. More specifically, FIG. 2 illustrates an example in which an optical fiber 18 acts as a surrogate for a target 30, and FIG. 3 illustrates an example in which an optical fiber 20 acts as a surrogate for the target 30 and OARs 32, 34. Additional surrogates (e.g., optical fibers and/or EM transponders) and/or dosimeters can additionally be implanted.

With reference to the example of FIG. 4, the EM transponders 22, 24 are implanted within the patient and act as surrogates for the target 30 and/or the OARs 32, 34. Further, the dosimeters 26, 28 generate dosimetric data for the target 30 and/or the OARs 32, 34. More specifically, FIG. 4 illustrates an example in which EM transponders 22, 24 act as surrogates for an OAR 34 and dosimeters 26, 28 generate dosimetric data for the OAR 34. Additional surrogates (e.g., optical fibers and/or EM transponders) and/or dosimeters can additionally be implanted (e.g., for an OAR 32 and/or the target 30).

Referring back, more generally, to FIGS. 2-4, in some embodiments, a wireless transmitter 40 is further implanted within the patient to transmit dosimetric data generated by the dosimeters 26, 28. Dosimetric data includes real-time transient or cumulative dosimetry. In such embodiments, the wireless transmitter 40 is suitably self-contained. In other words, it includes a power source, such as a battery.

The surrogates 18, 20, 22, 24 and/or the dosimeters 26, 28, as well as the wireless transmitter 40, can be directly affixed to one or more of the target 30, the OARs 32, 34, and the tissue proximate the target 30 and/or the OARs 32, 34. For example, the optical fibers 18, 20 can be wrapped around the target 30 and/or the OARs 32, 34. In some embodiments, however, at least some of the surrogates 18, 20, 22, 24, the dosimeters 26, 28, and the wireless transmitter 36 are affixed using a shrink wrap 42, typically a silk-based film, implanted within the patient, an example of which is illustrated in FIG. 4.

The shrink wrap 42 can wholly or partially cover the one or more of the target 30, the OARs 32, 34, and the tissue proximate the target 30 and/or the OARs 32, 34. For example, in prostate cancer, the shrink wrap 42 can be made to envelope the prostate or some combination of the prostate, bladder and rectum. Further, the shrink wrap 42 can be continuous and/or formed from a plurality of discrete patches 44, 45, 46, 47, 48. As to the former, the shrink wrap 42 can wrap around all or part of the target 30 and/or at least one of the OARs 32, 34. As to the latter, the wireless transmitter 40 is typically shared by the patches 44, 45, 46, 47, 48.

While any approach can be employed to implant the shrink wrap 42, the implantation of the shrink wrap 42 is typically carried out by collapsing the shrink wrap 42 and introducing it into the body by laparoscopic techniques (i.e., minimally invasive transperineal techniques). After navigating the shrink wrap 42 to the desired anatomical location under optical or other guidance, the shrink wrap 42 can be made to wrap or conform to the one or more of the target 30, the OARs 32, 34 and the tissue proximate to the target 30 and/or the OARs 32, 34 (either completely or partially). When the shrink wrap 42 is a silk-based film, this is performed by bringing it into contact with saline. The capillary forces at the biotic-abiotic interface will ensure a highly conformal wrap around the tissue.

The at least some of the surrogates 18, 20, 22, 24, the dosimeters 26, 28, and the wireless transmitter 40 can be affixed to the shrink wrap 42 prior to implantation and/or after implantation of the shrink wrap 42. As to the latter, implantation can be performed using laparoscopic techniques.

Referring back to FIG. 1, the planning system 16, in addition to receiving the planning images, typically receives dosimetric data and/or motion data. The planning system 16 receives the dosimetric data from the dosimeters 26, 28. Typically, the dosimetric data is received wirelessly from, for example, the wireless transmitter 40, but it is also contemplated that the dosimetric data is received from a physical connection to the dosimeters 26, 28. Further, the planning system 16 receives the motion data from one or more motion sensors 50 that employ the surrogates 18, 20, 22, 24 to generate the motion data. The motion sensors 50 can interface with the surrogates 18, 20, 22, 24 physically and/or wirelessly, depending upon the type of surrogates 18, 20, 22, 24.

For example, the motion sensors 50 typically interface with the optical fibers 18, 20 physically 18, 20 and the EM transponders 22, 24 wirelessly.

As shown in FIG. 2, a motion sensor 50 detachably connects to the optical fiber 18 to determine the location and shape of the optical fiber 18. The motion sensor includes a multispectrum light source 52 illuminating the optical fiber 18. Light is reflected by the mirror 36 of the optical fiber 18 and is directed by a beam splitter 54 to a light detector 56 and analyzed by an analyzer circuit 58. The analyzer circuit 58, through analysis of the reflected light, generates motion data indicating the location and shape of the optical fiber 18. The motion sensor 50 is exemplary of each of the motion sensors 50 which interface with optical fibers.

Using the planning images and, in some embodiments, the motion data and/or dosimetric data generated by the surrogates 18, 20, 22, 24 and/or the dosimeters 26, 28, respectively, the planning system 16 generates and/or updates treatment plans for the patients. In that regard, the planning system 16 can be employed for adaptive planning To facilitate treatment planning, the planning system 16 includes one or more of a segmentation module 60, a display module 62, an optimization module 64, a motion model 66, and a dosimetric module 68.

The segmentation module 60 is employed to identify and delineate regions in the planning images, including the target 30 and, optionally, the OARs 32, 34. If the planning images define a four-dimensional image set, the regions are identified and delineated in all phases of the planning images. The regions are typically delineated by contours surrounding the regions. Identification and delineation can be performed manually and/or automatically. As to the former, the segmentation module 60 cooperates with the display module 62 to allow clinicians to manually identify and delineate between the regions. As to the latter, computer algorithms can be employed.

In some embodiments, such as when the surrogates 18, 20, 22, 24 and/or the dosimeters 26, 28 are employed, the segmentation module 60 is further employed to identify and delineate the surrogates 18, 20, 22, 24 and/or the dosimeters 26, 28 in the planning images. If the planning images define a four-dimensional image set, the regions are identified and delineated in all phases of the planning images. The surrogates 18, 20, 22, 24 and/or the dosimeters 26, 28 can be delineated in the planning images using, for example, point-based markers and/or contours, depending upon the structural dimensions of the surrogates 18, 20, 22, 24 and/or the dosimeters 26, 28. For example, contours can be employed to delineate the optical fibers 18, 20 and point-based markers can be employed to delineate the dosimeters 26, 28 and/or the EM transponders 22, 24. As above, identification can be performed manually and/or automatically. As to the former, identification is carried out through cooperation with the display module 62. As to the latter, identification is carried out using computer algorithms.

One approach for automatically or semi-automatically identifying the surrogates 18, 20, 22, 24 in the planning images employs motion data. The patient is set up in a treatment couch 70 and, where applicable, the motion sensors 50 are connected to the surrogates 18, 20, 22, 24. For example, the motion sensors 50 are connected to the optical fiber 18. Motion data for the surrogates 18, 20, 22, 24 is then received and the location and/or shape of the surrogates 18, 20, 22, 24 are then determined on different planes (i.e., transverse, sagittal and coronal) using the motion data. The motion data is suitably collected temporally proximate to the generation of the planning images. Determining the location and/or shape of the surrogates 18, 20, 22, 24 vary depending upon the type of surrogate. However, the location of EM transponders can be determined using well known techniques, such as triangulation, and the location and shape of optical fibers can be determined using the fiber Bragg grating (FBG) principle.

Figure 5:
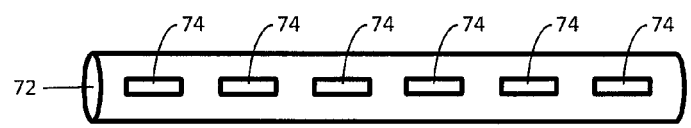
FIG. 5 illustrates an optical fiber and fiber Bragg gratings.

Any implementation of the FBG principle can be used, including, for example, wavelength-division multiplexed distributed sensing, time-wavelength-division multiplexed distributed sensing, interferometric detection, amplitude-based inherent scattering, and so on. For example, the shape of an optical fiber at any spatial location along its length is dependent on the internal strain developed in the fiber, and the Bragg wavelength is sensitive to this strain. Hence, the strain in three corresponding FBGs of like position and Bragg wavelength, one in each fiber of a group of three fibers, can be used to calculate local bend. Extending this to further groups of corresponding FBGs along the length of the fiber group using different Bragg wavelengths, local bend at numerous positions along the length of the fiber group are determined by the analyzer circuit 58. Combining the local bends with prior knowledge of the FBG positions along the length of the fiber group, the shape of the fiber group is estimated. With reference to FIG. 5, an optical fiber 72 with a plurality of FBGs 74 along its length is illustrated.

FBGs allow a spatial resolution of at least 40 μm and a temporal resolution of at least 200 Hz. Further, they allow an accuracy of less than or equal to 0.5 mm at a distance of 1 m from the source, which increases linearly as the distance from the source decreases. In contrast with EM tracking, optical fiber sensing is superior in both spatial and temporal resolution. The spatial resolution in EM tracking applications is typically very low due to the use of a limited number of EM transponders, such as three. Further, the temporal resolution of EM tracking is typically around 10 Hz and low when compared to optical fiber sensing. The tracking accuracy of EM tracking is typically around 1 mm.

Once the location and/or shape of the surrogates 18, 20, 22, 24 are identified, one or more transformations from the coordinate frames of the motion sensors 50 to the coordinate frame of the planning images are determined. Where there is a plurality of motion sensors, each with a different coordinate frame, a plurality of transformations corresponding to the motion sensors 50 are determined. The transformations are typically determined automatically using a registration algorithm. However, it is also contemplated that the transformations can be determined manually and/or semi-automatically. After determining the transformations, the location and/or shape of the surrogates 18, 20, 22, 24 are transformed to the coordinate frame of the planning images.

By identifying the location and/or shape of the surrogates 18, 20, 22, 24 in the planning images, a reference location and shape of the MS can be determined. As noted above, the shape of the MS is defined by the shape of the surrogates 18, 20, 22, 24 and/or the spatial relationship between the surrogates 18, 20, 22, 24. Where the surrogates 18, 20, 22, 24 include EM transponders, the shape of the MS is defined, at least partially, by the spatial relationships between the EM transponders. This spatial relationship defines an EM structure (EMS) of the MS. Where the surrogates include optical fibers, the shape of the MS is defined, at least partially, by the shape of each group of optical fibers. The shape of a group of optical fibers defines an optical fiber structure (OFS) of the MS.

In some embodiments, after identifying and delineating the surrogates 18, 20, 22, 24 and/or the dosimeters 26, 28 in the planning images, the spatial relationships between the surrogates 18, 20, 22, 24 and/or the dosimeters 26, 28, such as the optical fibers 18, 20, and the planning target volume (PTV) are determined. Similarly, after identifying and delineating the surrogates 18, 20, 22, 24 and/or the dosimeters 26, 28 in the planning images, the spatial relationships between the surrogates 18, 20, 22, 24 and/or the dosimeters 26, 28 and corresponding target and/or organs at risk are determined.

With reference again to FIG. 1, the display module 62 allows clinicians to at least one of generate, modify and view point-based markers and/or contours. In that regard, the display module 62 displays images and, in some embodiments, corresponding point-based markers and/or contours on a display device 76. Clinicians can then generate and/or modify point-based markers and/or contours on the images using one or more user input devices 78. For example, a clinician can employ a mouse to resize a contour or to move a point-based marker. Additionally or alternatively, the display module 62 allows clinicians to enter and/or define plan parameters, such as dose for contoured regions.

The optimization module 64 receives as input at least contours for the target 30 and/or the OARs 32, 34 and plan parameters, typically generated by the segmentation module 60 and/or the display module 62. The optimization module 64 optionally receives other relevant inputs, such as an attenuation map indicative of radiation absorption, cumulative motion patterns for the target 30 and/or the OARs 32, 34, delivered dose distributions, and so on. Based on the inputs, the optimization module 64 generates and/or updates a treatment plan complying with the plan parameters and any other relevant inputs. The treatment plan suitably includes a plurality of treatment fractions and a PTV to be irradiated. Treatment plans generated and/or updated by the optimization module 64 are suitably stored in one or more therapy memories 80.

In some embodiments, where motion data and/or dosimetric data are received, the optimization module 64 generates a treatment plan employing a hypofractionation scheme. For example, the hypofractionation scheme can span 5-6 treatment fractions, with each fraction assuming greater importance than in a typical fractionation scheme due to the higher magnitude of dose delivered per treatment fraction. The high temporal and spatial resolution of optical fiber sensing and/or the real-time dosimetry allows the collection of detailed information on target motion patterns and/or delivered dose distribution. This, in turn, allows for reduction in margins of treatment plans, which is important for hypofractionation, since motion-induced delivery errors, if any, will be higher in hypo fractionated schemes. The physical discomfort caused to patients due to the implantations, such as the optical fibers 18, 20, for the duration of the treatment plan will be minimal in comparison to standard treatment plans comprising 30-35 fractions.

The motion module 66, in some embodiments, works in conjunction with the other modules to facilitate the generation of a motion compensated treatment plan. The patient is set-up on the treatment couch 70, and, where applicable, the motion sensors 50 are connected to the surrogates 18, 20, 22, 24. For example, the motion sensors 50 are connected to the optical fiber 18. The location and shape of the MS is then periodically and/or continuously determined, as described above, for a predetermined period of time, such as 10 minutes. The clinician chooses the predetermined period of time, which is the amount of time the clinician deems necessary to observe the motion patterns of the patient. In some embodiments, the predetermined period of time is patient-specific.

For each determination, rigid motion of the MS is then estimated. Suitably, this includes comparing the determined location and shape of the MS to the reference location and shape of the MS to assess the motion therebetween. Rigid motion includes, for example, translations and rotations. In some embodiments, non-rigid motion is additionally or alternatively employed. The motion estimates are applied to the locations of each target or OAR in the planning images to yield motion compensated locations. A cumulative motion pattern, such as a probability density functions, for each target and/or OAR is determined by accumulating the motion-compensated locations therefor. The more determinations of the location and shape of the MS, the more accurate the cumulative motion patterns.

Once the cumulative motion patterns are generated, they are provided to the optimization module 64 to generate and/or update a treatment plan. For example, the optimization module 64 employs the cumulative motion patterns to plan motion compensated dose distributions for each treatment fraction. Motion compensated dose distributions can be generated by convolving planned dose distribution with the corresponding cumulative motion patterns. For example, the dose distribution for a fraction is convolved with the cumulative motion pattern corresponding to the target to be irradiated.

The motion module 66, in some embodiments, further works in conjunction with the other modules to facilitate the generation of a motion compensated estimate of the dose delivered to a patient. The patient is set-up on the treatment couch 70, and, where applicable, the motion sensors 50 are connected to the surrogates 18, 20, 22, 24. While executing the treatment plan, the location and shape of the MS is determined, as discussed above, periodically and/or continuously. Fraction-specific cumulative motion patterns are then generated for each target and/or OAR, as discussed above. In some embodiments, the cumulative motion patterns take in to account samples collected before treatment delivery.

The cumulative motion patterns are then convolved with corresponding planned dose distributions. For example, a cumulative motion pattern for a fraction is convolved with the planned dose distribution for the fraction. The motion compensated dose distributions are then accumulated to get the motion compensated estimate of the dose delivered to the patient. It is contemplated that the motion compensated estimate can be determined during the execution of a treatment plan or after the execution of a treatment plan. Insofar as the motion compensated estimate is determined during the execution of a treatment plan, the cumulative motion patterns for current fractions are convolved with planned dose distributions adjusted for the amount of the fraction that has been executed.

The motion compensated estimate of the dose delivered to the patient can be employed for post treatment analysis. For example, the estimated or delivered dose distribution can be compared to the planned dose distribution. Further, the motion compensated estimate of the dose delivered to the patient can be employed to facilitate the updating of treatment plans. For example, the motion compensated estimate of delivered dose distribution can be passed to the optimization module 64 for re-optimization of the treatment plan. It is contemplated that updating can be performed in real time during the execution of a treatment fraction, after a treatment fraction, or at any other point during the execution of a treatment plan.

The dosimetric module 68 can be employed to determine an estimate of deliver dose distribution. During the delivery of treatment fractions, the dosimetric module 68 receives real-time dosimetric data from the dosimeters 26, 28. It is contemplated that the dosimetric data can be received continuously and/or periodically during treatment fractions. Using the known locations of the dosimeters in the planning images, an estimate of delivered dose distribution can be made. It is also contemplated that the estimate can be compensated for motion, as discussed above.

The estimate of delivered dose distribution can be employed for post-treatment analysis. By comparing the planned dose distribution with the estimate of the delivered dose distribution, the efficacy of the dose delivery can be determined. The estimate of the delivered dose distribution can also be employed for generating and/or updating treatment plans. For example, the estimate of delivered dose distribution can be passed to the optimization module 64 for re-optimization of the treatment plan. It is contemplated that updating can be performed in real time during the execution of a treatment fraction, after a treatment fraction, or at any other point during the execution of a treatment plan.

The dosimetric module 68 can further be employed to correlate, during treatment fractions, motion data from the motion sensors 50 with dosimetric data from the dosimeters 26, 28. For example, an estimate of delivered dose distribution and a corresponding location and shape of the MS can be determined one or more of continuously, a predetermined number of times during a treatment fraction and at a predetermined rate during a treatment fraction. The estimates and the current locations and shapes can then be correlated using, for example, time stamps.

Using the correlated estimates and current locations and shapes, organ positions that result in maximum dosimetric deviations from the treatment plan can be determined. For example, the current locations and shapes of the MS can be used to generate motion compensated estimates of delivered dose distributions. These motion compensated estimates of delivered dose distribution can then be compared with the planned dose distributions to determine organ positions that result in maximum dosimetric deviations. By summing the dosimetric deviations over at least one of the correlated sets (typically a plurality) and thresholding or ranking from high to low the summations, the organ positions that result in maximum dosimetric deviation can be determined.

Using the correlated estimates and current locations and shapes, the patient-specific relationship between particular motion patterns and the resulting dosimetric deviations from the original treatment plan can also be determined. The relationship allows the generation and/or updating of treatment plans that are sensitive to those motion patterns that produce unacceptable dosimetric deviations.

The organ positions and/or the patient-specific relationships can be used by the optimization module 64 for the generation and/or updating of treatment plans. For example, the organ positions and/or the patient-specific relationships can be added to a database and used for improving the generation and/or updating of treatment plans for the corresponding patients and/or similar patients. Similarity can be assessed based on demographics and/or locality, such as region, nation, and so on.

At a scheduled day and time for a therapy session of a patient, a therapy delivery apparatus 82 delivers therapy to the patient. The therapy, such as ablation therapy and/or brachytherapy, can include radiation involving one or more of x-rays, protons, high-intensity focused ultrasound (HIFU), and the like. Suitably, the therapy delivery apparatus 82 is controlled by a therapy control system 84 in accordance with a treatment plan, optionally as updated between treatment fractions and/or during treatment fractions. The therapy treatment plan can be received from, for example, the therapy memories 80.

In some embodiments, the therapy control system 84 includes an alignment module 86 to facilitate the alignment of patients to the coordinate frame of corresponding treatment plans using motion data and/or dosimetric data received from the motion sensors 50 and/or the dosimeters 26, 28. It is contemplated that alignment is performed off-line, for example, before a treatment fraction, and/or in real-time, for example, during a treatment faction. Additionally or alternatively, the therapy control system 84 includes a safety module 88 facilitating the suspension of a treatment fraction when a patient gets out of alignment.

To facilitate the alignment of patients to the coordinate frame of corresponding treatment plans, the patient is set-up on the treatment couch 70, and, where applicable, the motion sensors 50 are connected to the surrogates 18, 20, 22, 24. The current location and shape of the MS is determined, as discussed above. The current location and shape can be determined in response to an event, such as an event triggered by a user input device 90 or a periodic timer, or continuously. Typically, when the alignment is performed off-line, the current location and shape of the MS are typically determined once. Further, typically, when the alignment is performed in real-time, the current location and shape of the MS is determined periodically or continuously.

Upon determining the current location and shape of the MS, the current location and shape are compared and matched with the reference location and shape of the MS. The comparison can be performed automatically and/or manually. As to the latter, the current location and shape and the reference location and shape can be graphically represented on a display device 92. In some embodiments, the graphical representations are overlaid and/or coded using, for example, different colors, line patterns, etc. When the current location and shape of the MS is periodically or continuously determined, the graphical representations are likewise periodically or continuously updated.

Additionally, or alternatively, to facilitate the alignment of patients in real-time while carrying out treatment fractions, current delivered dose distributions, determined as described above, from dosimetric data of the dosimeters 26, 28 are compared with planned dose distributions. A current delivered dose distribution can be determined in response to an event, such as an event triggered by a user input device 90 or a periodic timer, or continuously. The comparison can be performed automatically and/or manually. As to the latter, the current dose distribution and the planned dose distribution can be graphically represented on the display device 92. In some embodiments, the graphical representations are overlaid and/or coded using, for example, different colors, line patterns, etc. When the current dose distribution is periodically or continuously determined, the graphical representations are likewise periodically or continuously updated.

Deviations between the current location and shape of the MS and the reference location and shape of the MS and/or deviations between the current dose distribution and the planned dose distribution are an indication that the target 30 and/or the OARs 32, 34 have moved from their location in the planning image. This can be due to patient motion, such as breathing, or because the patient has become misaligned on the treatment couch 70. Significant and recurring deviations may be indicative of a need for re-imaging and re-planning. Accordingly, the patient is realigned based on the comparison. In some embodiments, audio and/or visual cues as to how to realign the patient are provided. For example, a visual cue may be displayed on the display device 92 indicating the patient needs to be moved left. Further, in some embodiments, the patient is automatically realigned. This can include moving the treatment couch 70 or the therapy delivery apparatus 82 delivering the therapy. In both cases, one or more of electric motors, hydraulics, and so on can be employed.

To facilitate the suspension of a treatment fraction when a patient gets out of alignment, the current location and shape of the MS and the planning location and shape of the MS are manually or automatically compared, as discussed above. Additionally, or alternatively, the current delivered dose distributions, determined as described above, from dosimetric data of the dosimeters 26, 28 are compared with planned dose distributions. When a manual comparison is performed, it falls to the clinician administering the treatment fraction to suspend it using the user input device 90. Assuming an automatic comparison is performed, the treatment fraction can be suspended manually or automatically when the deviation exceeds a threshold set by a clinician administering the therapy. The threshold is proportional to risk of harming the patient, failing to deliver the planned dose to the target 30 or OARs 32, 34, and the like. In some embodiments, the clinician sets the threshold at the level of risk they deem acceptable. In other embodiments, the threshold is variable based on the dose map. For example, if motion in a certain direction is less critical than another, the threshold can be larger in that direction. As to manual suspension, audio and/or visual cues as to when to suspend the fraction are contemplated. For example, a visual cue may be displayed on the display device 92 indicating the fraction needs to be suspended via the user input device 90.

In some embodiments, spatial relationships between the planned target and/or OARs and the current target and/or organs at risk. The current location and shape of the target 30 and the OARs 32, 34 is determined from the current location and shape of the MS. If the spatial relationships deviate beyond a predetermined threshold, the treatment fraction is suspended. The predetermined threshold is suitably set by a clinician and is proportional to risk of irradiating the OARs or under dosing the target. Hence, the clinician sets the predetermined threshold at the maximum level of risk allowed. Advantageously, such a spatial comparison, allows for intervention if the target are deemed to exit the PTV or if the OARs enter the PTV.

The therapy beam is focused on the planned location of the target 30 and/or the OARs 32, 34. Breathing and other forms of patient motion cause the actual location of the target 30 and/or the OARs 32, 34 to differ from the plan. For example, the target 30 move partially or fully out of the radiation beam and the OARs 32, 34 move partially or fully in to the radiation beam. The target and OAR locations are determined from the current location and shape of the MS. In one embodiment, the radiation beam is gated off whenever the target 30 move partially out of the beam or the OARs 32, 34 moves partially into the beam beyond preset tolerances. When the target 30 moves back into the beam trajectory or the OARs 32, 34 move out of the beam trajectory, the beam is gated back on. In another embodiment, rather than ON/OFF gating, the intensity of the radiation beam is modulated. In another embodiment, the radiation beam trajectory is adjusted in real time to stay focused on the target 30 and avoid the OARs 32, 34.

The beam intensity and one or more of: (1) an estimate of the delivered dose distribution determined using dosimetric data; and (2) a current location and shape of the MS (and hence the locations of the target 30 and the OARs 32, 34) determined using motion data, are supplied to the planning system 16 to calculate a delivered dose distribution depicting the radiation dose actually delivered to the target 30 and/or the OARs 32, 34 during the treatment fraction. By comparing the delivered dose distribution to the planned dose distribution, the planning system 16 calculates adjustment to the treatment plan for the subsequent fractions or the remaining portion of the same fraction.

The planning system 16 and the therapy control system 84 include one or more memories 94, 96 and one or more processors 98, 100. The memories 94, 96 store executable instructions for carrying out the functions associated with the planning system 16 and the therapy control system 84, including those associated with the segmentation module 60, the display module 62, the optimization module 64, the motion module 66, the dosimetric module 68, the alignment module 86 and the safety module 88. The processors 98, 100 execute the executable instructions stored on the memories 94, 96. In certain embodiments, the planning system 16 and/or the therapy control system 84 include communication units 102, 104 for communicating with, for example, each other, the image memories 14, the therapy memories 80, and so on, via a communications network and/or a data bus, such as a local area network or the Internet.

After delivery of a treatment plan, the implants, such as the surrogates 18, 20, 22, 24, the dosimeters 26, 28 and the wireless transmitter 40, are removed from the patient. This can be performed using laparoscopic techniques (i.e., minimally invasive transperineal techniques). Where the shrink wrap 42 is employed, the shrink wrap 42 is typically biodegradable such that it does not need to be removed. However, insofar as it is not biodegradable, it is removed with the implants.

Figure 6:
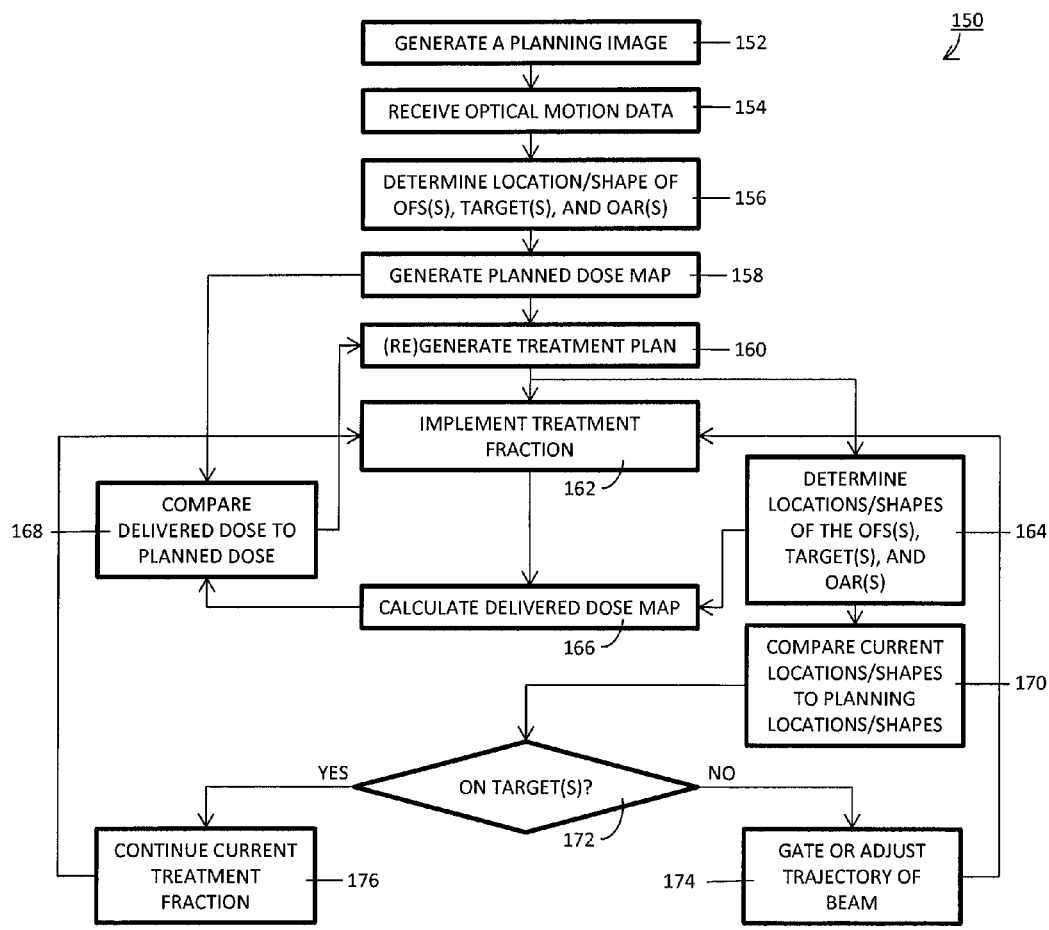
FIG. 6 illustrates a method of estimating interfraction and intrafraction motion using optical fibers.

With reference to FIG. 6, a method 150 for therapy planning using a MS comprised of a OFS is provided. The processors 98, 100 of the planning system 16 and/or the therapy control system 84 suitably perform the method 150. One or more planning images of a target and/or one or more OARs are generated 152 from, for example, the imaging modalities 12. Optical motion data indicative of location and shape of at least one optical fiber implanted within the patient is further received 154 from, for example, the motion sensors 50. The at least one optical fiber acts as a surrogate for the target and/or the OARs. The spatial relationships between the OFS on the planning image and the optical motion data are determined 156. The locations, shapes and spatial correspondence of the target and/or the OARs are determined from these relationships.

Based on the planning images and, optionally, the location and shape of the OFS, a planning dose map and treatment plan are generated 158, 160 using, for example, the optimization module 64. A treatment fraction of the generated treatment plan is then implemented 162 using the therapy delivery apparatus 82 to deliver the planned dose of therapy, usually radiation therapy. Further, while implementing the treatment fraction, the locations and shapes of the current OFS, target and OARs are determined 164 using optical motion data.

In some embodiments, the determined locations and shapes are used in conjunction with the planned dose map and the treatment plan to calculate 166 a delivered dose map taking in to account motion during the implementation of the treatment fraction. The delivered dose map is compared 168 to the planned dose map and employed to regenerate 160 the treatment plan during delivery of the treatment plan. Further, in some embodiments, the determined locations and shapes are further compared 170 to the planning locations and shapes and a determination 172 as to whether the therapy beam is on the target is made. If the therapy beam is not on the target, the radiation beam is gated 174 off until it is back on the target or the trajectory of the beam is adjusted 174 appropriately. If the therapy beam is on the target, the current treatment fraction continues 176.

Figure 7:
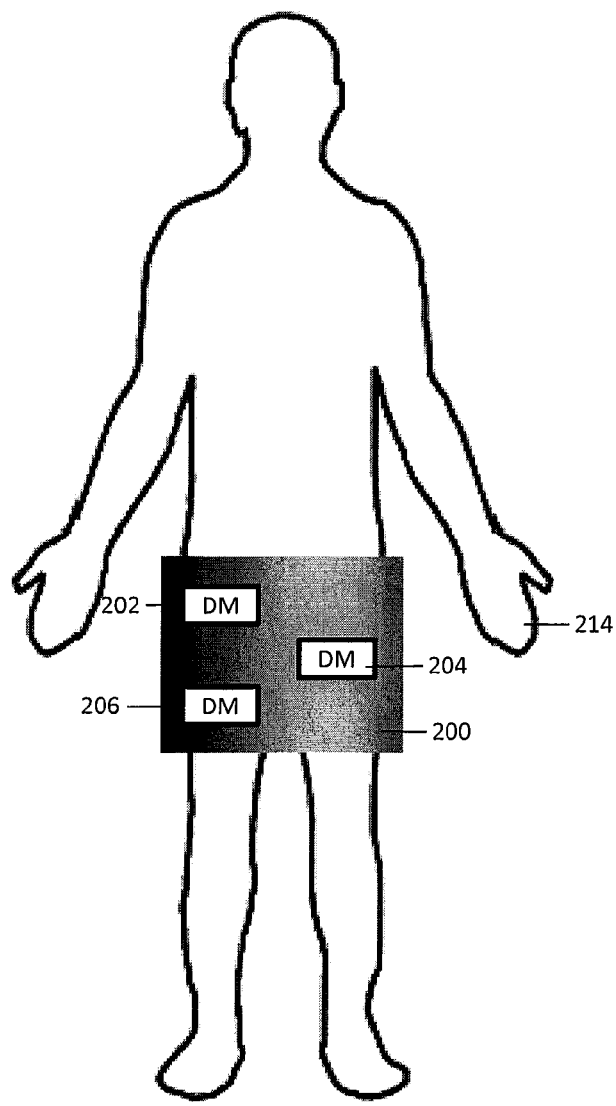
FIGS. 7 and 8 illustrate a constellation of dosimeters on a vest worn by a patient.
Figure 8:
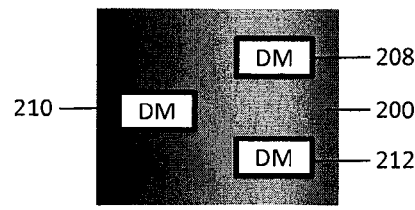

With reference to FIGS. 7-8, a vest 200 equipped with one or more dosimeters 202, 204, 206, 208, 210, 212 is fitted to a patient 214. "Vest", as used herein, connotes a construction that is adherable to the patient, such as a garment, wrap or the like. FIG. 7 illustrates a first side of the vest 200 from a first view point. FIG. 8 illustrates a second side of the vest 200, opposite the first side, from a view point opposite the view point of FIG. 7. The vest 200 can be substantially any shape, such as belt shaped (illustrated).

The dosimeters 202, 204, 206, 208, 210, 212 of the vest 200 are substantially the same as the implanted dosimeters 26, 28 of FIGS. 1-5. Further, the vest 200 is suitably employed with the therapy system 10 of FIGS. 1-5. Within the therapy system 10, dosimetric data generated by the implanted dosimeters 26, 28 can be substituted for dosimetric data generated by the dosimeters 202, 204, 206, 208, 210, 212 of the vest 200. Hence, dosimetric data from the dosimeters 202, 204, 206, 208, 210, 212 of the vest 200 can be employed for patient set-up and localization and/or adaptive treatment planning and delivery. In contrast to the implanted dosimeters 26, 28, the dosimeters 202, 204, 206, 208, 210, 212 of the vest 200 advantageously require no pre-treatment invasive procedures.

Typically, the dosimeters 202, 204, 206, 208, 210, 212 of the vest 200 include one or more pairs to measure the entry and exit dose of a specific radiation beam emanating from the therapy delivery apparatus 82 (shown in FIG. 1), such as a linear particle accelerator (LINAC). Further, each pair typically includes dosimeters on opposing sides of the vest 200, such as the front and the back. For example, as illustrated in FIGS. 7 and 8, a dosimeter 202 is paired with a dosimeter 208, a dosimeter 204 is paired with a dosimeter 210, and a dosimeter 206 is paired with a dosimeter 212. The dosimeters 202, 204, 206, 208, 210, 212 that are diametrically opposite may need to be paired, since beams can typically be at any angle between the anterior-posterior and left-right orthogonal directions. Using the vest 200, the therapy control system 84 ensures that the planned dose is accurately delivered to the patient. For example, the alignment module 86 and the safety module 88 of FIGS. 1-5 can employ dosimetric data generated by the dosimeters 202, 204, 206, 208, 210, 212 of the vest 200.

The vest 200 and/or the positioning of the dosimeters 202, 204, 206, 208, 210, 212 can be tailored to the target 30 and/or the OARs 32, 34 of a patient 214. For example, one or more dosimeters, typically one or more pairs, can be grouped into constellations corresponding to the target 30 and/or the OARs 32, 34. Constellations can then be tailored to the corresponding target and/or the OARs. In the example, of FIGS. 7 and 8, a first constellation is tailored to the prostate of the patient 214. To facilitate customization to the patient 214, the dosimeters 202, 204, 206, 208, 210, 212 are typically removably connected to the vest 200. For example, the dosimeters 202, 204, 206, 208, 210, 212 can be connected to the vest 200 using, for example, Velcro and/or mechanical fasteners. It is also contemplated that the dosimeters 202, 204, 206, 208, 210, 212 can be secured to the vest 200 via a system of interlocking tracks that allow the dosimeters to easily slide from one position to another.

As noted above, the dosimeters 202, 204, 206, 208, 210, 212 are typically arranged to measure the entry and/or exit dose of radiation beams. Hence, the dosimeters 202, 204, 206, 208, 210, 212 are typically arranged to coincide with the beam directions from the therapy delivery apparatus 82. To determine the location of the dosimeters 202, 204, 206, 208, 210, 212, the off-line alignment procedure, described above, is employed. Namely, the coordinate frame of the therapy delivery apparatus 82 is registered with the coordinate frame of the planning images. Using this registration, any pose of a radiation beam can be accurately mapped on to the space of the planning images. Hence, the exact positions of the entry and the exit of each beam can be mapped on to the patient's body and may be used for positioning of the dosimeters 202, 204, 206, 208, 210, 212. Positioning of the dosimeters 202, 204, 206, 208, 210, 212 can be performed automatically and/or manually. As to the former, the dosimeters 202, 204, 206, 208, 210, 212 can be connected to motors that position the dosimeters 202, 204, 206, 208, 210, 212 appropriately. For example, the motors can slide the dosimeters 202, 204, 206, 208, 210, 212 along tracks in the vest 200.

If the placement of dosimeters 202, 204, 206, 208, 210, 212 in the path of the beam is a concern due to reduction in dose received by the target, then the dosimeters 202, 204, 206, 208, 210, 212 can be placed only in the exit path of each beam. Further, only one dosimeter for the exit path of the currently active beam, or only one pair of dosimeters for the entry and exit paths of the current active beam, are contemplated. The dosimeter(s) can be connected to a motor that slides or otherwise positions the dosimeter(s) along the vest 200 to position it as desired, depending on the angular position of the currently-active beam. The coordinate frame of the motor can be registered to that of the therapy delivery apparatus 82 using well known techniques.

Figure 9:
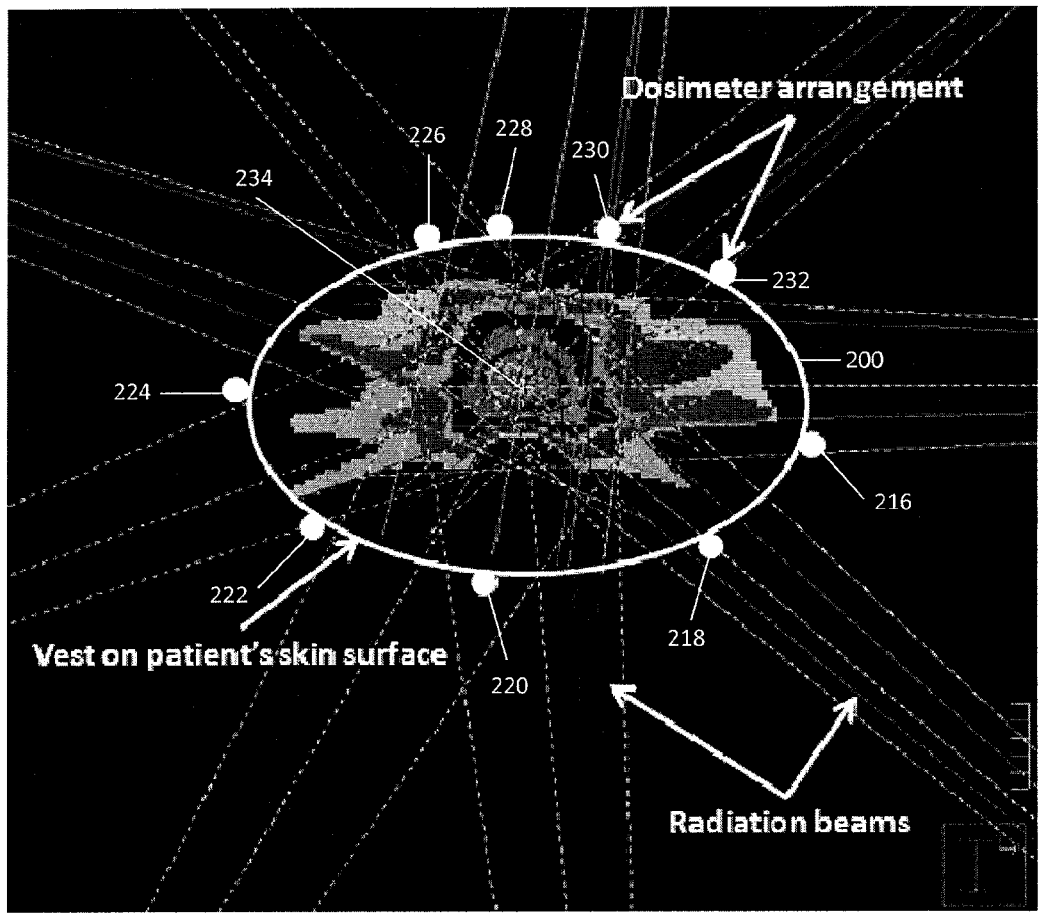
FIG. 9 illustrates an arrangement of dosimeters on a vest worn by a patient and beam directions.

With reference to FIG. 9, another example of the vest 200 is provided. The vest 200 is positioned around a target prostate of a patient to be treated. The vest includes dosimeters 216, 218, 220, 222, 224, 226, 228, 230, 232. Further, beam directions are superimposed on a two transverse view of a prostatic dose plan 234, where the dosimeters 216, 218, 220, 222, 224, 226, 228, 230, 232 are positioned in the exit path of each beam. The different colors of the prostatic dose plan 234 correspond to different dose levels, where the dose level increases from the periphery of the prostatic dose plan 234 to the center of the prostatic dose plan 234. During delivery of the prostatic dose plan, the dosimeters 216, 218, 220, 222, 224, 226, 228, 230, 232 measure the dose entering and exiting the patient. Using the known beam directions and known locations of the dosimeters 216, 218, 220, 222, 224, 226, 228, 230, 232, the dose delivered to the target prostate can be determined, as described above.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. For example, the planning system 16 and the therapy control system 84 can be the same system. It is intended that the invention be construed as including all such modifications and alterations insofar as they come within the scope of the appended claims or the equivalents thereof.

Having thus described the preferred embodiments, the invention is now claimed to be:

1. A therapy system comprising:
at least one processor programmed to:
receive a planning image of a region of a subject, the subject including a target and/or an organ at risk (OAR), and the subject being associated with at least one surrogate acting as a surrogate for the target and/or the OAR, wherein the subject surrogate includes an implanted optical fiber which defines an optical fiber structure (OFS), the surrogate being the implanted optical fiber;
determine a reference location and shape in the planning image for one or more of the target and/or the OAR;
determine a reference location and/or shape from the planning image of each of the surrogate;
determine deviations between:
the reference location and/or shape of the surrogate and a current location and/or shape of the surrogate.

2. The therapy system according to claim 1, further including:
a dosimeter implanted within the subject and secured to at least one of the target, the OAR and tissue proximate the target and/or the OAR and/or the OFS, and wherein the one or more processors is further programmed to determine deviations between a planned dose distribution and a delivered dose distribution, the delivered dose distribution determined from dosimetric data and the reference location and/or shape of the dosimeter.

3. The therapy system according to claim 2, wherein the subject includes the surrogate and the processor is further programmed to:
determine the reference location and/or shape for the surrogate;
receive motion data indicating the current location and/or shape of the surrogate; and,
determine deviations between the reference location and/or shape of the surrogate and the current location and/or shape of the surrogate.

4. The therapy system according to claim 3, wherein the processor is further programmed to:
determine a current location and shape of the target and/or the OAR in the planning image from deviations between the reference location and shape of the surrogate and the current location and shape of the surrogate; and,
determine deviations between the current location and shape of the target and/or the OAR and the reference location and shape of the target and/or the OAR.

5. The therapy system according to claim 3, wherein the processor is further programmed to:
receive motion data indicating a current location and/or shape in the planning image for the surrogate during delivery of therapy; and,
one or more of:
based on deviations of the surrogate, adjust the treatment plan on which the delivery of the therapy is based; and,
generate a motion compensated estimate of radiation delivered to the target and/or the OAR from the motion data.

6. The therapy system according to claim 1, wherein the processor is further programmed to:
receive a plurality of motion data samples and/or a plurality of dosimetric data samples over a predetermined period of time, each of the motion data samples indicting a location and/or shape in the planning image for the surrogate, and each of the dosimetric data samples indicating dose delivered to the target and/or the OAR; and,
one or more of:
generate a cumulative motion pattern for the target and/or the OAR from the plurality of motion data samples; and,
through correlation and analysis of the plurality of motion data samples and the plurality of dosimetric data samples, one or more of:
determine a position of the target and/or the OAR with maximum dosimetric deviation; and,
determine a patient-specific relationship between motion patterns and dosimetric deviations.

7. The therapy system according to claim 1, wherein the processor is further programmed to:
receive reference optical motion data indicating a reference location and shape of the OFS;
determine the reference location and shape of the OFS in the planning image from the reference optical motion data;
receive current optical motion data indicating a current location and shape of the OFS;
determine the current location and shape of the OFS in the planning image from the current optical motion data; and,
determine deviations between the determined reference location and shape of the OFS and the determined current location and shape of the OFS.

8. The therapy system according to claim 1, wherein the subject includes a dosimeter and the processor is further programmed to:
determine the reference location and/or shape for the dosimeter;
receive dosimetric data indicating dose delivered to the target and/or the OAR from the dosimeter; and,
determine deviations between the planned dose distribution and the delivered dose distribution.

9. The therapy system according to claim 8, wherein the processor is further programmed to:
receive dosimetric data indicating dose delivered to the target and/or the OAR from the dosimeter during delivery of therapy; and,
one or more of:
in response to deviations between the planned dose distribution and the delivered dose distribution being beyond select criteria, stop delivery of therapy;
based on deviations of the planned dose distribution and the delivered dose distribution, align the subject in the treatment couch; and,
based on deviations of the planned dose distribution and the delivered dose distribution, adjust a treatment plan on which the delivery of therapy is based.

10. The therapy system according to claim 1, wherein the deviations are used for delivery of therapy, the therapy including one of ablation therapy, brachytherapy, x-ray therapy, proton therapy, and high-intensity focused ultrasound (HIFU) therapy.

11. A therapy system comprising:
at least one processor programmed to:
receive a planning image of a region of a subject, the subject including a target and/or an organ at risk (OAR), and the subject being associated with an optical fiber and the optical fiber acting as a surrogate for the target and/or the OAR;
determine a reference location and shape in the planning image for one or more of the target and/or the OAR;
determine a reference location and/or shape from the planning image of the optical fiber;
wherein one or more of: (1) the reference location and/or shape of the optical fiber; and (2) the current location and/or shape of the optical fiber, are determined using fiber Bragg gratings of different Bragg wavelengths along the length of the optical fiber, and;
determine deviations between the reference location and/or shape of the surrogate and a current location and/or shape of the surrogate.

12. The therapy system according to claim 11, further comprising:
a vest including a dosimeter, the dosimeter positioned on the vest to coincide with beam directions of a therapy delivery apparatus.

13. A therapy system comprising:
a structure configured to carry one or more dosimeters, the dosimeters configured to be implanted in a subject to measure dose delivered to a target and/or an organ at risk (OAR) of the subject;
shrink wrap configured to be implanted with and secure in the dosimeter directly or indirectly to at least one of the target, the OAR, and tissue proximate to the target and/or OAR; and,
at least one processor programmed to:
receive dosimetric data indicating dose delivered to the target and/or the OAR from the dosimeters; and,
determine deviations between a planned dose distribution and a delivered dose distribution, the delivered dose distribution determined from the dosimetric data.

14. The therapy system according claim 13, further including:
a surrogate mounted to the structure and configured to be implanted and secured by the shrink wrap.

15. The therapy system according to claim 14, wherein the surrogate includes an optic fiber.

16. The therapy system according to claim 13, wherein the processor is further programmed to:
one or more of:
in response to deviations between the planned dose distribution and the delivered dose distribution being beyond select criteria, stop delivery of therapy;
based on deviations of the planned dose distribution and the delivered dose distribution, align the subject in a treatment couch;
and, based on deviations of the planned dose distribution and the delivered dose distribution, adjust a treatment plan on which the delivery of therapy is based.

17. A method for therapy planning comprising:
receiving a planning image of a region of a subject, the subject including a target and/or an organ at risk (OAR), and the subject associated with a surrogate and a dosimeter, the surrogate acting as a surrogate for the target and/or the OAR, and the dosimeter measuring dose delivered to the target and/or the OAR, wherein the surrogate includes an optic fiber structure;
implanting the optic fiber structure and the dosimeter in the subject proximate to the target and/or the OAR;
determining a reference location and shape in the planning image for one or more of the target and/or the OAR;
determining a reference location and/or shape from the planning image of each of the surrogate and/or the dosimeter; and
determining deviations between one or more of:
the reference location and/or shape of the surrogate and a current location and/or shape of the surrogate; and, a planned dose distribution and a delivered dose distribution, the delivered dose distribution determined from dosimetric data and the reference location and/or shape of the dosimeter.

18. The method according to claim 17, further including: receiving one or more of:
   motion data indicating a current location and/or shape in the planning image for the surrogate; and,
   dosimetric data indicating dose delivered to the target and/or the OAR from the dosimeter.

19. The method according to claim 17, further including: determining a current location and/or shape of the optical fiber using fiber Bragg gratings of different Bragg wavelengths along the length of the optical fiber.

20. The method according to claim 17, further including: securing the surrogate and the dosimeter adjacent to the target and/or the OAR using shrink wrap.

21. A therapy system comprising:
   at least one processor programmed to:
   receive a planning image of a region of a subject, the subject including a target and/or an organ at risk (OAR), and the subject being associated with at least one surrogate and/or a dosimeter, the surrogate acting as a surrogate for the target and/or the OAR, and the dosimeter measuring dose delivered to the target and/or the OAR, wherein the surrogate and/or the dosimeter are configured to be implanted within the subject and secured indirectly to the at least one of the target, the OAR and tissue proximate the target and/or the OAR using a shrink wrap;
   determine a reference location and shape in the planning image for one or more of the target and/or the OAR;
   determine a reference location and/or shape from the planning image of each of the surrogate and/or the dosimeter;
   determine deviations between one or more of:
      the reference location and/or shape of the surrogate and a current location and/or shape of the surrogate; and,
      a planned dose distribution and a delivered dose distribution, the delivered dose distribution determined from dosimetric data and the reference location and/or shape of the dosimeter.

* * * * *